United States Patent

Oyama et al.

[11] Patent Number: 6,117,434
[45] Date of Patent: Sep. 12, 2000

[54] HUMECTANT COMPOSITION, BASE CONTAINING THE SAME, AND COSMETIC MATERIAL OR EXTERNAL PREPARATION CONTAINING SAID HUMECTANT COMPOSITION

[75] Inventors: Keiichi Oyama; Toshie Narita; Masaaki Fujisawa, all of Yokohama; Naoko Tsuchiya, Yokosuka; Misako Tsuji, Ayase, all of Japan

[73] Assignee: The Nisshin Oil Mills Ltd., Tokyo, Japan

[21] Appl. No.: 09/068,671

[22] PCT Filed: Sep. 24, 1996

[86] PCT No.: PCT/JP96/02739

§ 371 Date: May 14, 1998

§ 102(e) Date: May 14, 1998

[87] PCT Pub. No.: WO98/13436

PCT Pub. Date: Apr. 2, 1998

[51] Int. Cl.$^7$ ........................................................ A61K 7/00
[52] U.S. Cl. ........................... 424/401; 424/450; 514/937; 514/938; 514/944
[58] Field of Search ..................... 424/401, 450; 514/944, 937, 938

[56] References Cited

U.S. PATENT DOCUMENTS 5,456,915  10/1995  Nagase et al. ........................... 424/401
5,709,849   1/1998  Ito et al. .................................... 424/63

FOREIGN PATENT DOCUMENTS 08119846  5/1996  Japan .
08183726  7/1996  Japan .
08183727  7/1996  Japan .

*Primary Examiner*—José G. Dees
*Assistant Examiner*—Michael A. Williamson
*Attorney, Agent, or Firm*—Nixon & Vanderhye

[57] ABSTRACT

A moisturizing composition comprising a trihydric or more water soluble polyhydric alcohol, lecithin and 3-methyl-1,3-butylene glycol, wherein lecithin:the trihydric or more water soluble polyhydric alcohol+3-methyl-1,3-butylene glycol=1:1,000 to 1:1 (weight ratio) and the trihydric or more water soluble polyhydric alcohol:3-methyl-1,3-butylene glycol=1:10 to 20:1 (weight ratio), various bases containing the moisturizing composition, and a cosmetic or external preparation containing the moisturizing composition. The moisturizing composition, bases, and cosmetic and external preparation are excellent in moisturizing properties, and have good stability.

9 Claims, No Drawings

HUMECTANT COMPOSITION, BASE CONTAINING THE SAME, AND COSMETIC MATERIAL OR EXTERNAL PREPARATION CONTAINING SAID HUMECTANT COMPOSITION

TECHNICAL FIELD

This invention relates to a moisturizing composition, a base containing the same, and a cosmetic or external preparation containing the moisturizing composition.

BACKGROUND ART

It is well-known that moisture is deeply involved in various products such as cosmetics, pharmaceuticals, agricultural chemicals and foods, and moisturization thereof is one of important functions for the quality of the products. It is also well-known that moisture is deeply involved in the retention of youthful skin, and the moisturization of skin is one of important functions for the quality of cosmetics.

As known moisturizing agents, particularly known moisturizing agents used in cosmetics or external preparations, there are polyhydric alcohols such as glycerol, 1,3-butylene glycol and sorbitol, and further pyrrolidonecarboxylate salts, lactate salts, etc. In recent years, sodium hyaluronate produced by a microorganism has come to be used.

Moisturizing agents also play an important role to work as an agent retaining the moisture of cosmetics or external preparations themselves and thereby contribute to the retention of the stability of the system. Trihydric or more polyhydric alcohols such as glycerol and sorbitol have excellent moisturizing properties and moisture retainability, and further in view of their safety, stability, prices, etc., are used as most general purpose moisturizing agents.

As to requirements which moisturizing agents should have, it is desirable that they are not influenced by environmental conditions (temperature, humidity, wind, etc.), and particularly can retain moisture for a long time regardless of the surrounding humidity. However, in the case of any moisturizing agent, the amounts of the absorption and release of moisture are influenced by the surrounding humidity because of its vapor pressure. In the case of glycerol, for instance, its equilibrium moisture content at 25° C. is 60% when the relative humidity is 75%, and 15% when the relative humidity is 33%, and in the case of sorbitol, its equilibrium moisture content at 25° C. is 50% when the relative humidity is 75%, and 5% when the relative humidity is 33%, and their moisture contents are influenced by the degree of the surrounding relative humidity.

Thus, there is a problem that when the surrounding humidity is low, the moisturizing agent itself releases the retaining moisture and the amount of moisture retained is lowered. Also when cosmetics or external preparations containing moisturizing agents are used, as understood from the above, moisture is lost from the skin with time lapse under low humidities, and the moisturizing function is lowered. Therefore, as to moisturizing agents, it is necessary that the evapotranspiration of moisture under low humidity environments is slow.

DISCLOSURE OF INVENTION

This invention has been made in view of the above problems, and aims to provide a moisturizing composition excellent in moisturizing properties and stability, bases based thereon, and a cosmetic or external preparation containing the moisturizing composition.

The above object has been attained by (1) a moisturizing composition comprising a trihydric or more water soluble polyhydric alcohol, lecithin and 3-methyl-1,3-butylene glycol, wherein lecithin:the trihydric or more water soluble polyhydric alcohol+3-methyl-1,3-butylene glycol=1:1,000 to 1:1 (weight ratio) and the trihydric or more water soluble polyhydric alcohol:3-methyl-1,3-butylene glycol=1:10 to 20:1 (weight ratio), (2) A viscous or gel-like base which comprises the moisturizing composition of the above (1) having compounded therein an oily substance.

(3) An oil-in-water type emulsion base which comprises the moisturizing composition of the above (1) having compounded therein an oily substance and water.

(4) A solubilized base which comprises the moisturizing composition of the above (1) diluted with water.

(5) A cosmetic which comprises the moisturizing composition of the above (1) and other raw material(s) for cosmetics.

(6) An external preparation which comprises the moisturizing composition of the above (1) and other raw material(s) for external preparations.

In the above, the moisturizing composition can further contain water in an amount of more than 0% by weight but up to 50% by weight of the total weight of the trihydric or more water soluble polyhydric alcohol, lecithin and 3-methyl-1,3-butylene glycol. For displaying remarkable moisturizing properties, the moisturizing composition desirably has polarizability. The above trihydric or more water soluble polyhydric alcohol is preferably glycerol and/or sorbitol. The lecithin is preferably hydrogenated lecithin in view of oxidation stability.

The invention is further detailedly described below.

As lecithin constituting the moisturizing composition of the invention, there can be used soybean lecithin or egg yolk lecithin, before all else, which is available as a usual commercial product or reagent, and purified lecithin or fractionated lecithin obtainable by subjecting soybean lecithin or egg yolk lecithin to purification operation(s) such as solvent fractionation, extraction and/or fractionation to remove neutral oily matter as sufficiently as possible, or the like. For rapidly dissolving lecithin in a trihydric or more water soluble polyhydric alcohol, purified lecithin wherein neutral oily matter is removed is preferred. Lecithin constituting the moisturizing composition of the invention is assumed to further include hydrogenated lecithin and lysolecithin. Lecithin, in many cases, has an unsaturated fatty acid chiefly at the 2-position of glycerol constituting it, and one obtained by converting it, at least partially, to a saturated fatty acid is hydrogenated lecithin. The degree of hydrogenation in the hydrogenated lecithin is not particularly limited, but it is desirable in view of oxidation stability that it is 45 to 100%, preferably 80 to 100%. Preferred as lysolecithin is one having a low hydrolysis degree, i.e. deacylation degree (e.g., one having a hydrolysis degree of 70% or less). Lysolecithin having a high hydrolysis degree (e.g., one having a hydrolysis degree of more than 70%) can also be used in the invention, but when used, it is preferred to use it together with usual lecithin and make the mixing ratio of such lysolecithin 80% by weight or less based on the usual lecithin. As lecithin used in the invention including even hydrogenated lecithin and lysolecithin, such lecithin that the fatty acid constituting it is not a single fatty acid (ones derived from nature as exemplified above fall under this category) is preferred, and synthetic phosphatidylcholine having a single fatty acid as an constituent is undesirable because when it is used in place of the lecithin in the moisturizing composition of the invention, there is a tendency that precipitate deposits.

The trihydric or more water soluble polyhydric alcohol constituting the moisturizing composition of the invention is not particularly limited, and there can be used, as representative ones, glycerol, sorbitol, diglycerol, triglycerol, polyglycerol, erythritol, pentaerythritol, glucose, galactose, fructose, sucrose, maltose, xylose, xylobiose, reduced oligosaccharides, etc. These can be used alone or in combination of two or more. Preferred among them are glycerol and sorbitol.

As to 3-methyl-1,3-butylene glycol constituting the moisturizing composition of the invention, it is convenient to utilize commercial products (e.g., one made by KURARAY CO., LTD.). A composition comprising 3-methyl-1,3-butylene glycol, a trihydric or more water soluble polyhydric alcohol and lecithin (the moisturizing composition of the invention), whose characteristic lies in containing 3-methyl-1,3-butylene glycol, has a remarkably enhanced moisturizing characteristic, compared with a composition not containing 3-methyl-1,3-butylene glycol (usual compositions), as illustrated in the later-described examples and comparative examples.

In the moisturizing composition of the invention, it is necessary that the ratio (weight ratio) of lecithin:the trihydric or more water soluble polyhydric alcohol+3-methyl-1, 3-butylene glycol is 1:1,000 to 1:1, and the ratio is preferably 1:200 to 1:1, more preferably 1:50 to 1:2. When the weight ratio of lecithin to the trihydric or more water soluble polyhydric alcohol+3-methyl-1,3-butylene glycol is less than 1/1,000, the moisturizing properties of the moisturizing composition is insufficient, and when the ratio is more than 1/1, the lecithin cannot uniformly dissolve in the composition and insoluble matter deposits.

In the moisturizing composition of the invention, it is also necessary that the ratio (weight ratio) of the trihydric or more water soluble polyhydric alcohol:3-methyl-1,3-butylene glycol is 1:10 to 20:1, and the ratio is preferably 1:7 to 20:1, more preferably 1:4 to 10:1. When the amount of 3-methyl-1,3-butylene glycol is larger than that of the case where the weight ratio of the trihydric or more water soluble polyhydric alcohol:3-methyl-1,3-butylene glycol is 1:10, a tendency enlarges that the lecithin cannot stably dissolve in the trihydric or more water soluble polyhydric alcohol and precipitate is formed at room temperature (e.g., 20° C.) to a low temperature (e.g., 5° C.). When the amount of 3-methyl-1,3-butylene glycol is smaller than that of the case where the weight ratio is 20:1, the moisturizing composition of the invention does not become high viscous and moisturizing characteristics do not come to a satisfiable degree.

The moisturizing composition of the invention can be substantially nonaqueous, or can further contains water in an amount of more than 0 weight % but up to 50 weight % of the total weight of the trihydric or more water soluble polyhydric alcohol, lecithin and 3-methyl-1,3-butylene glycol. Usually, in commercial lecithins, water of the order of 0.1 to 3% by weight is contained, and in trihydric or more water soluble polyhydric alcohols, 0.1% by weight or more water is contained (among commercial products, there are even water-containing products such as glycerol having a water content of 0.1 to 20% by weight and sorbitol having a water content of 30% by weight), and in 3-methyl-1,3-butylene glycol, water of the order of 0.1 to 2% by weight is contained. Therefore, in preparation of a moisturizing composition of the invention which contains water, there is a case where water does not need to be added. When the trihydric or more water soluble polyhydric alcohol is a solid saccharide or sugar alcohol (sucrose, glucose, fructose, sorbitol, etc.), it is desirable to add water in an amount of about 10% by weight to about 50% by weight of the total weight of the trihydric or more water soluble polyhydric alcohol, lecithin and 3-methyl-1,3-butylene glycol and uniformly dissolve the solid.

It is preferred that the moisturizing composition of the invention has polarizability. By making the moisturizing composition of the invention a composition having polarizability, it comes to exhibit remarkable moisturizing characteristics.

It is surmised that when the moisturizing composition of the invention contains water or water is compounded into the composition, by the interaction of the coexisting respective components, lecithin takes a specific association structure and high viscous liquid crystals are formed, and thereby the evapotranspiration of water from the composition is inhibited.

There is no particular limitation about processes for preparing the moisturizing composition of the invention, but the composition can be prepared, for example, by stirring a trihydric or more water soluble polyhydric alcohol, lecithin and 3-methyl-1,3-butylene glycol, and, when needed, water, if necessary under heating, to make the mixture a uniform solution.

The invention also relates to a viscous or gel-like base which comprises the moisturizing composition of the invention having compounded threrein an oily substance. This viscous or gel-like base can be used as a base for viscous or gel-like products on which moisturizing properties are needed.

As the oily substance, there can be used, without particular limitation, hydrocarbons, esters, fats or oils, waxes, higher fatty acids, higher alcohols, silicone substances, sterols, resin saccharides, etc. As examples of them, there can be mentioned liquid petrolatum, isoparaffin, petrolatum, squalane, isopropyl myristate, octyldodecyl myristate, cetyl isooctylate (cetyl 2-ethylhexanoate), glyceryl triisooctylate (glyceryl tri-2-ethylhexanoate), glyceryl tricaprylate, diisooctylic acid neopentyl glycol ester (di-2-ethylhexanoic acid neopentyl glycol ester), diisostearyl malate, isononyl isononanoate (3,5,5-trimethylhexanoic acid 3,5,5-trimethylhexyl alcohol ester), cholesteryl 12-hydroxystearate, mono- to hexaisostearic acid dipentaerythritol esters using isostearic acid made by Emery Industries, Inc., isooctyl o, m or p-methoxycinnamate, eucalyptus oil, soybean oil, cotton seed oil, sesame oil, rice germ oil, rice bran oil, safflower oil, sunflower seed oil, palm oil, olive oil, jojoba oil, macadamia nuts oil, avocado oil, castor oil, evening primrose oil, turtle oil, mink oil, orange roughy oil, lanolin, myristic acid, palmitic acid, stearic acid, oleic acid, 12-hydroxystearic acid, behenic acid, stearyl alcohol, oleyl alcohol, cetanol, lanolin alcohol, paraffin wax, microcrystalline wax, ceresin wax, beeswax, carnauba wax, candelilla wax, shellac wax, soybean hardened oil, rapeseed hardened oil, glyceryl tristearate, rosin, cholesterol, phytosterol, dimethyl polysiloxane, methyl phenyl polysiloxane, essential oil components originated in animals or plants, etc. They can be used alone or in combination of two or more.

In the viscous or gel-like base of the invention, it is suitable that the compounding amount of the oily substance is more than 0 times by weight but up to 10 times by weight, preferably 0.001 to 5 times by weight the total amount of the trihydric or more water soluble polyhydric alcohol, lecithin and 3-methyl-1,3-butylene glycol in the moisturizing composition. When the compounding amount is more than 10 times by weight, the moisturizing composition separates.

There is no particular limitation about processes for preparing the viscous or gel-like base of the invention, and it can, for example, be obtained by compounding the oily substance into the moisturizing composition under stirring.

The viscous or gel-like base of the invention can be used as a base for various viscous or gel-like products. AS such viscous or gel-like products, there can be mentioned cosmetics (creams, cleansing gel, moisture gel, etc.), external preparations (ointments, etc.), agricultural chemicals, etc.

The invnention also relates to an oil-in-water type emulsion base which comprises the moisturizing composition of the invention having compounded threrein an oily substance and water. As the oily substance used in this oil-in-water type emulsion base, there can be used the same oily substances as described in the viscous or gel-like base of the invention, and its compounding amount can also be the same as therein.

It is suitable that the total compounding amount of water in the oil-in-water type emulsion base of the invention is 0.1 to 100 times by weight, preferably 0.1 to 20 times by weght the total amount of the water soluble polyhydric alcohol, lecithin and 3-methyl-1,3-butylene glycol in the moisturizing composition. When the compounding amount is less than 0.1 times by weght, the resultant base does not become an oil-in-water state, and when it is more than 100 times by weight, the effects of the invention cannot be expected. It is possible to previously compound, into this water, water soluble or dispersible component(s) such as known surfactant(s) or moisturizing agent(s).

There is no particular limitation about processes for preparing the oil-in-water type emulsion base of the invention, and it can, for example, be obtained by compounding the oily substance and water into the moisturizing composition under stirring, or by compounding water into the above viscous or gel-like base under stirring.

The oil-in-water type emulsion base of the invention can be used as a base for oil-in-water type emulsion preparations, etc. As such oil-in-water type emulsion preparations, there can be mentioned cosmetics (liquid cream, cream, skin lotion, etc.), etc.

The invention also relates to a solubilized base which comprises the moisturizing composition of the invention diluted with water. It is suitable that the total compounding amount of water in this solubilized base is 0.5 to 100 times by weght, preferably 0.5 to 20 times by weght the total amount of the water soluble polyhydric alcohol, lecithin and 3-methyl-1,3-butylene glycol in the moisturizing composition. When the compounding amount is less than 0.5 times by weight, the resultant base does not become a solubilized state, and when it is more than 100 times by weight, the effects of the invention cannot be expected. It is possible to previously compound, into this water, water soluble or dispersible component(s) such as known surfactant(s) or moisturizing agent(s). There is no particular limitation about processes for preparing the solubilized base of the invention, and it can, for example, be obtained by adding water to the moisturizing composition under stirring. The solubilized base of the invention can be used as a base for solubilized aqueous products which are expected to have moisture retainability. As such aqueous products, there can be mentioned cosmetics (skin lotions, cosmetic essences, etc.), etc.

The invention still further relates to a cosmetic which comprises the moisturizing composition according of the invention and other raw material(s) for cosmetics.

This cosmetic includes creams, liquid creams, skin lotions, cosmetic essences, cleansing gels, and further includes skin care cosmetics such as moisture gels and packs, and makeup cosmetics to which moisturizing effect is expected such as emulsion type foundations, emulsion eye shadows and nail treatments.

As the other raw materials for cosmetics, there can be mentioned oily substances (the same ones as in the viscous or gel-like base of the invention), surfactants (anionic, cationic, nonionic, amphoteric), mucilaginous substances (or water soluble macromolecules) (tragacanth gum, quince seed gum, xanthane gum, sodium alginate, cellulose derivatives, polyvinyl alcohol, sodium polyacrylate, carboxyvinyl polymers, polyethylene oxide, bentonite, etc.), powders (talc, kaolin, zinc white, titanium dioxide, mica, precipitated calcium carbonate, heavy calcium carbonate, calcium secondary phosphate, etc.), medicines (vitamins, hormones, antihistaminics, astringents, amino acids, etc.), ultraviolet absorbers, sequestering agents (EDTA sodium salt, etc.), other moisturizing agents (sodium hyaluronate, etc.), antioxidants, pH-adjusting agents, pigments and dyes, perfumes, antiseptics, water, etc. These other raw materials for cosmetics can be used alone or in combination of two or more.

It is suitable that the rate of the moisturizing composition in the cosmetic is 1 to 95% by weight, preferably 2 to 90% by weight in terms of the total content of the trihydric or more water soluble polyhydric alcohol, lecithin and 3-methyl-1,3-butylene glycol in the cosmetic. When the rate is less than 1% by weight, the effects of the invention cannot be expected.

There is no particular limitation about processes for preparing the cosmetic of the invention, and it can, for example, be prepared by compounding at least one of the oily substance and water, and other raw materials for cosmetics into the moisturizing composition under stirring.

The invention also relates to an external preparation which comprises the moisturizing composition of the invention and other raw material(s) for external preparations.

This external preparation includes quasi-drugs, and lotion-like external preparations, ointments, gel agents, etc. which are medicines, for skin inflammations accompanied by the dryness of the skin such as chaps, cracks, itches and atopic dermatitis.

The other raw materials for external preparations include pharmaceutically effective ingredients and base components for external preparations.

As the base components for external preparations, there can be mentioned oily substances (the same ones as in the viscous or gel-like base of the invention), surfactants (anionic, cationic, nonionic, amphoteric), mucilaginous substances (or water soluble macromolecules) (tragacanth gum, quince seed gum, xanthane gum, sodium alginate, cellulose derivatives, polyvinyl alcohol, sodium polyacrylate, carboxyvinyl polymers, polyethylene oxide, bentonite, etc.), powders (talc, kaolin, zinc white, titanium dioxide, mica, precipitated calcium carbonate, heavy calcium carbonate, calcium secondary phosphate, etc.), pH-adjusting agents, antiseptics, colorants, water, etc. These other raw materials for external preparations can be used alone or in combination of two or more.

It is suitable that the rate of the moisturizing composition in the external preparation is 1 to 95% by weight, preferably 2 to 90% by weight in terms of the total content of the trihydric or more water soluble polyhydric alcohol, lecithin and 3-methyl-1,3-butylene glycol in the external preparation. When the rate is less than 1% by weight, the effects of the invention cannot be expected.

There is no particular limitation about processes for preparing the external preparation of the invention, and it can, for example, be prepared by compounding a pharmaceutically effective ingredient and base component(s) for external preparations into the moisturizing composition under stirring.

EXAMPLES

The invention is specifically described below by examples and comparative examples.

Examples 1 to 8

Glycerol and/or sorbitol, purified hydrogenated soybean lecithin (BASIS LS-60H, made by THE NISSHIN OIL MILLS, LTD.) and 3-methyl-1,3-butylene glycol (made by KURARAY CO., LTD.) were used. These components were mixed so that the lecithin content could be 5:95 (weight ratio) in terms of the lecithin:glycerol and/or sorbitol+3-methyl-1,3-butylene glycol and the ratio between glycerol and/or sorbitol and 3-methyl-1,3-butylene glycol could be the prescribed weight ratios, the mixtures were made into solutions by heating to 80° C., and the solutions were cooled to room temperature to give moisturizing compositions of the invention. Then, 20 g of each of the compositions was heated again to 80° C., 10 g of purified water of the same temperature was mixed, followed by sufficient stirring. After cooled to room temperature, the mixtures were put in Petri dishes, respectively, and left alone in a room adjusted to a temperature of 25° C. and a relative humidity of 30%, and the amounts of water reduction were measured with time lapse. The results are shown in Table 1.

In all the compositions of the invention, it was revealed that the rates of water reduction are slower than those in the later-described comparative examples, and thus the compositions of the invention are excellent in moisture retainability and useful as moisturizing compositions.

TABLE 1

(unit: g)

| Example | Ratio of the components in the composition (weight ratio) | Amount of water reduction (lapse time: hr) | | |
|---|---|---|---|---|
| | | 6 | 12 | 24 |
| 1 | Glycerol:3-M-1,3-BG = 1:10 | 0.26 | 0.52 | 0.86 |
| 2 | Glycerol:3-M-1,3-BG = 1:4 | 0.29 | 0.54 | 0.90 |
| 3 | Glycerol:3-M-1,3-BG = 1:1 | 0.32 | 0.59 | 0.95 |
| 4 | Glycerol:3-M-1,3-BG = 3:1 | 0.38 | 0.68 | 0.99 |
| 5 | Sorbitol:3-M-1,3-BG = 1:10 | 0.15 | 0.26 | 0.43 |
| 6 | Sorbitol:3-M-1,3-BG = 1:1 | 0.16 | 0.28 | 0.47 |
| 7 | Sorbitol:3-M-1,3-BG = 20:1 | 0.21 | 0.40 | 0.63 |
| 8 | Glycerol/Sorbitol (= 1/1): 3-M-1,3-BG = 1:1 | 0.24 | 0.44 | 0.71 |

Note) 3-M-1,3-BG: 3-methyl-1,3-butylene glycol, which is applied as well hereinafter Examples 9 to 14

Moisturizing compositions were prepared according to the process mentioned in Example 1 under the condition that the same raw materials were used as in Example 1, glycerol:3-methyl-1,3-butylene glycol was made to be 1:1 (weight ratio) and the lecithin (=purified hydrogenated soybean lecithin) contents were made so as to be the prescribed values. Thereafter, under the same method and conditions as in Example 1, the amounts of water reduction from mixtures of 20 g each of the moisturizing compositions with 10 g each of water were measured, respectively (see Table 2).

In all the compositions, it was revealed that the rates of water reduction are slower than those in the later-described comparative examples, and thus the compositions are suitable as moisturizing compositions.

TABLE 2

(unit: g)

| Example | Lecithin:glycerol + 3-M-1, 3-BG in the composition (% by weight) | Amount of water reduction (lapse time: hr) | | |
|---|---|---|---|---|
| | | 6 | 12 | 24 |
| 9 | 0.1:99.9 | 0.92 | 1.18 | 1.60 |
| 10 | 0.5:99.5 | 0.54 | 0.81 | 1.29 |
| 11 | 2.5:97.5 | 0.38 | 0.69 | 1.13 |
| 12 | 10:90 | 0.24 | 0.42 | 0.67 |
| 13 | 20:80 | 0.12 | 0.17 | 0.23 |
| 14 | 30:70 | 0.07 | 0.10 | 0.14 |

Comparative Examples 1 to 8

The same experiments as in Example 1 were carried out under the condition of no addition of lecithin (see Table 3). It was revealed that in all the compositions, the rates of water reduction are large, and thus in the compositions the amounts of the retained water are liable to be influenced by the surrounding humidity.

TABLE 3

(unit: g)

| Comparative example | Ratio of the components in the composition (weight ratio) | Amount of water reduction (lapse time: hr) | | |
|---|---|---|---|---|
| | | 6 | 12 | 24 |
| 1 | Glycerol:3-M-1,3-BG = 1:4 | 0.84 | 1.44 | 2.05 |
| 2 | Glycerol:3-M-1,3-BG = 1:1 | 1.27 | 1.87 | 2.51 |
| 3 | Glycerol:3-M-1,3-BG = 3:1 | 1.00 | 1.63 | 2.32 |
| 4 | Sorbitol:3-M-1,3-BG = 1:1 | 0.88 | 1.43 | 2.07 |
| 5 | Glycerol alone | 1.00 | 1.76 | 2.37 |
| 6 | 3-M-1,3-BG alone | 0.87 | 1.44 | 2.10 |
| 7 | Glycerol:propylene glycol = 1:1 | 1.28 | 1.98 | 2.62 |
| 8 | Glycerol:1,3-butylene glycol = 1:1 | 1.00 | 1.68 | 2.41 |

Comparative Examples 9 to 11

The same experiments as in Example 1 were carried out under the condition that 3-methyl-1,3-butylene glycol was not used or alternative glycol was used instead of it, and the lecithin (=purified hydrogenated soybean lecithin) content was made to be lecithin:glycerol or glycerol+alternative glycol=5:95 (weight ratio) (see Table 4). It was revealed that also in the compositions of these examples, the rates of water reduction are large, and thus in the compositions the amounts of the retained water are liable to be influenced by the surrounding humidity.

TABLE 4

(unit: g)

| Comparative example | Ratio of the components in the composition (weight ratio) | Amount of water reduction (lapse time: hr) | | |
|---|---|---|---|---|
| | | 6 | 12 | 24 |
| 9 | Glycerol alone | 0.92 | 1.98 | 2.29 |
| 10 | Glycerol:propylene glycol = 1:1 | 1.05 | 1.43 | 2.11 |
| 11 | Glycerol:1,3-butylene glycol = 1:1 | 0.91 | 1.43 | 2.14 |

Examples 15 to 16 and Comparative Examples 12 to 13

Compositions were prepared according to the process mentioned in Example 1 under the condition that the same raw materials were used as in Example 1, glycerol:3-methyl-1,3-butylene glycol was made to be 1:1 (weight ratio) and the lecithin (=purified hydrogenated soybean lecithin) contents in the composition were made to be 5:95 (weight ratio) (Examples 15 and 16) or 0 (Comparative examples 12 and 13) in terms of lecithin:glycerol+3-methyl-1,3-butylene glycol. 20 g each of the compositions and the prescribed amount of purified water (5 g or 20 g) were mixed, and under the same method and conditions as in Example 1, the amounts of water reduction from the mixtures were measured, respectively (see Table 5).

TABLE 5

(unit: g)

| | Lecithin:glycerol + 3-M-1,3-BG in the composition (weight ratio) | Amount of water in the mixture (g) | Amount of water reduction (lapse time: hr) | | |
|---|---|---|---|---|---|
| | | | 6 | 12 | 24 |
| Example | | | | | |
| 15 | 5:95 | 5 | 0.11 | 0.21 | 0.35 |
| 16 | 5:95 | 20 | 0.60 | 1.20 | 2.08 |
| Comparative example | | | | | |
| 12 | Lecithin content | 5 | 0.42 | 0.74 | 1.08 |
| 13 | Lecithin content 0 | 20 | 1.23 | 2.41 | 4.22 |

Examples 17 to 22 and Comparative Examples 14 to 18

Moisturizing compositions having the prescribed compositions were prepared, water was added to each of the compositions, and, in order to check the resultant mixtures for stability at room temperature (20° C.) and a low temperature (5° C.), the states of the mixtures after a lapse of 24 hours at these temperatures were observed, respectively. The mixtures were also checked for the presence of polarizability at 60° C., 20° C. and 5° C. using a polarization microscope. The results are shown in Table 6. It was revealed from Table 6 that the compositions according to the invention are excellent in stability at room temperature and the low temperature. It was also revealed that all the compositions according to the invention have polarizability.

TABLE 6

(unit: % by weight)

| Component | Example | | | | | | Comparative example | | | | |
|---|---|---|---|---|---|---|---|---|---|---|---|
| | 17 | 18 | 19 | 20 | 21 | 22 | 14 | 15 | 16 | 17 | 18 |
| Purified hydrogenated soybean lecithin | 10 | 5 | 40 | 25 | | | 10 | 10 | 45 | | |
| Purified soybean lecithin | | | | | 30 | | | | | 20 | |
| Egg yolk lecithin | | | | | | 10 | | | | | 10 |
| Glycerol | 30 | 20 | 30 | | 40 | | 30 | 30 | 20 | 40 | 40 |
| Sorbitol 70[1] | | | | 30 | | 60 | | | | | |
| 3-Methyl-1,3-butylene glycol | 30 | 40 | 20 | 30 | 30 | 20 | | | 20 | | |
| Ethanol | | | | | | | 30 | | 30 | | |
| Hexylene glycol | | | | | | | | 30 | | | 40 |
| Water | 30 | 35 | 10 | 15 | | 10 | 30 | 30 | 15 | 10 | 10 |
| Stability[2] | | | | | | | | | | | |
| (20° C.) | o | o | o | o | o | o | x | x | x | o | o |
| (5° C.) | o | o | o | o | o | o | x | x | x | x | x |
| Presence of polarizability | | | | | | | | | | | |
| (60° C.) | yes | yes | yes | yes | no | no | no | no | yes | no | no |
| (20° C.) | yes | yes | yes | yes | yes | yes | — | — | — | no | no |
| (5° C.) | yes | yes | yes | yes | yes | yes | — | — | — | — | — |

Note
[1] An aqueous solution containing 70% by weight sorbitol
[2] Evaluation of stability; there is no deposit: o, there are deposits: x On the mixtures of each of the compositions of Examples 3 and 6 and Comparative examples 2, 4, 7, 8, 10 and 11 among the above-mentioned examples and comparative examples with water, the presence of polarizability and viscosities (measured by a BL-type viscometer) were as shown in Table 7.

As seen from this, one of the characteristics of the compositions of the invention is that they become a remarkably high viscous state by the addition of water.

TABLE 7

| | Presence of polarizability | Viscosity (CPS/25° C.) |
|---|---|---|
| Example | | |
| 3 | yes | 3500 |
| 6 | yes | 3250 |
| Comparative example | | |
| 2 | no | 20 |
| 4 | no | 17 |
| 7 | no | 12 |
| 8 | no | 17 |
| 10 | yes | 78 |
| 11 | yes | 177 |

Example 23

25 g of glycerol, 3 g of purified hydrogenated soybean lecithin (BASIS LP-20H, made by THE NISSHIN OIL MILLS, LTD.), 9 g of 3-methyl-1,3-butylene glycol (made by KURARAY CO., LTD.) and 1 g of water were mixed, and heated to 80° C. for dissolution to give a moisturizing composition as a uniform solution. Separately, 62 g of a mixture of squalane and liquid petrolatum in equal volume as an oily substance was heated to 80° C. and added by portions to the above composition under stirring at the same temperature. The mixture was cooled to room temperature to give a gel-like base. When this base was left alone for 6 months in a room (20 to 25° C., relative humidity: 30 to 50%), there was almost no change in its moisture content and the base was stable without forming any deposit.

Example 24

15 g of an aqueous 70% by weight sorbitol solution, 1 g of purified hydrogenated egg yolk lecithin (Lipoid E-80-3 made by Lipoid Co.), 10 g of 3-methyl-1,3-butylene glycol (the same one as in Example 23) were mixed, and heated to 80° C. for dissolution to give a moisturizing composition as a uniform solution. Separately, 15 g of olive oil and 5 g of paraffin wax were mixed and heated to 85° C. to give an oily substance as a solution. The oily substance was added by portions to the above composition at 80° C. under stirring to give a viscous composition, and 54 g of water of the same temperature was added to this to give an emulsion, and the emulsion was cooled to room temperature to give an oil-in-water type emulsion base. This base was filled into a vessel and it was checked for stability under the same condition as in Example 23, and as a result the base retained its stable emulsified state without separating an oil phase or an aqueous phase.

Example 25

30 g of diglycerol/fructose=1/1 (weight), 20 g of purified soybean lecithin (BASIS LS-60 made by THE NISSHIN OIL MILLS, LTD.), 40 g of 3-methyl-1,3-butylene glycol (made by KURARAY CO., LTD.) and 10 g of water were mixed, and heated to 80° C. for dissolution to give a moisturizing composition as a uniform solution. 70 g of water was added by portions to 30 g of the above composition at the same temperature to give a solubilized base. This base retained its stable state for 6 months in a room (20 to 25° C., relative humidity: 35 to 45%) without forming any precipitate and becoming white turbid.

Example 26

Samples (liquid cream type model cosmetics) were prepared according to the following basic formulations (see Table 8). The surfaces of skins coated respectively with each of the samples were measured for conductance, and thereby the moisturizing effect of each sample on the skin was evaluated.

Process of Preparing Such a Sample

The component A was mixed into the component B under stirring at a temperature of 80° C., the component C was added by portions, purified water was added to make the mixture emulsified, and the emulsion was cooled to 20° C.

Method of measuring the conductance of the skin surface

The medial part of the brachium of a female normal person was cleaned with ethanol, 0.02 g of a sample was applied onto a region thereon of a radius of 3 cm. At the time of a lapse of 60 minutes, the part was measured for conductance in a room of a temperature of 19 to 21° C. and a relative humidity of 30 to 40% using a high frequency conductance measuring apparatus (IB-355 type made by IBS Co.). Measured values were expressed as an avarage value on 3 subjects.

The formulation of each sample and the measured value of the conductance of the surface of the skin coated with each sample are shown in Table 8. As seen therefrom, in each of the model cosmetics of the invention (Sample Nos. 1 to 3 and 8 to 11), the conductance of the skin surface became a large value, and thus its excellent moisturizing effect on the skin was revealed. On the other hand, in the model cosmetics wherein 3-methyl-1,3-butylene glycol was not used (Sample Nos. 4 to 7) and in the model cosmetics wherein lecithin was not used together (Sample Nos. 12 to 16), the conductances were small and their moisturizing effects were weak.

TABLE 8

(Compounding amounts of components: % by weight)

| | Sample No. | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| | Invention product | | | Comparative product | | | | Invention product | | | | Comparative product | | | | |
| Component A | | | | | | | | | | | | | | | | |
| Purified hydrogenated soybean lecithin[1] | 5 | 5 | 5 | 5 | 5 | 5 | 5 | 0.5 | 1 | 2 | 10 | | | | | |
| Tween 80[2] | | | | | | | | | | | | 1 | 1 | 1 | 1 | 1 |
| Span 80[3] | | | | | | | | | | | | 1 | 1 | 1 | 1 | 1 |
| Component B | | | | | | | | | | | | | | | | |
| Glycerol | 10 | 5 | 15 | 20 | 10 | 10 | | 10 | 10 | 10 | 10 | 10 | 20 | 10 | 10 | |
| 3-M-1,3-BG[4] | 10 | 15 | 5 | | | | | 10 | 10 | 10 | 10 | 10 | | | | |
| 1,3-Butylene glycol | | | | | 10 | | | | | | | | | 10 | | |
| Propylene glycol | | | | | | 10 | | | | | | | | | | 10 |
| Component C | | | | | | | | | | | | | | | | |
| Olive oil | 10 | 10 | 10 | 10 | 10 | 10 | 10 | 10 | 10 | 10 | 10 | 10 | 10 | 10 | 10 | 10 |
| Cetanol | 2 | 2 | 2 | 2 | 2 | 2 | 2 | 2 | 2 | 2 | 2 | 2 | 2 | 2 | 2 | 2 |

TABLE 8-continued (Compounding amounts of components: % by weight)

| | Sample No. | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| | Invention product | | | Comparative product | | | | Invention product | | | | Comparative product | | | | |
| Purified water | 63 | 63 | 63 | 63 | 63 | 63 | 83 | 67.5 | 67 | 66 | 58 | 66 | 66 | 66 | 66 | 86 |
| Conductance of skin sunface ($\mu\Omega^{-1}$) | 212 | 208 | 202 | 90 | 92 | 95 | 70 | 150 | 165 | 180 | 243 | 85 | 80 | 81 | 85 | 55 |

[1])BASIS LS-60-H, made by THE NISSHIN OIL MILLS, LTD.
[2])Sorbitan monooleate ethylene oxide adduct, made by Tokyo Kasei Co., Ltd.
[3])Sorbitan monooleate, made by Tokyo Kasei Co., Ltd.
[4])3-Methyl-1,3-butylene glycol, made by KURARAY CO., LTD.

Example 27

Samples (skin lotion type model cosmetics) were prepared according to the following basic formulations (see Table 9). The surfaces of skins coated respectively with each of the samples were measured for conductance, and thereby the moisturizing effect of each sample on the skin was evaluated.

Process of Preparing Such a Sample

The component A was mixed into the component B under stirring at a temperature of 80° C., purified water containing a certain pH-adjusting agent was added by portions, and the mixture was cooled to 20° C.

Method of Measuring the Conductance of the Skin Surface

The same as in Example 26

The formulation of each sample and the measured value of the conductance of the surface of the skin coated with each sample are shown in Table 9. As seen therefrom, in each of the model cosmetics of the invention (Sample Nos. 1 to 3 and 8 to 11), the conductance of the skin surface became a large value, and thus its excellent moisturizing effect on the skin was revealed. On the other hand, in the model cosmetics wherein 3-methyl-1,3-butylene glycol was not used (Sample Nos. 4 to 7) and in the model cosmetics wherein lecithin was not used (Sample Nos. 12 to 18), the conductances were small and their moisturizing effects were weak.

TABLE 9

(Compounding amounts of components: % by weight)

| | Sample No. | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| | Invention product | | | Comparative product | | | | Invention product | | | | Comparative product | | | | | | |
| Component A | | | | | | | | | | | | | | | | | | |
| Purified hydrogenated soybean lecithin[1]) | 5 | 5 | 5 | 5 | 5 | 5 | 5 | 0.5 | 1 | 2 | 10 | | | | | | | |
| Component B | | | | | | | | | | | | | | | | | | |
| Glycerol | 10 | 5 | 15 | 20 | 10 | 10 | | 10 | 10 | 10 | 10 | 10 | 5 | 15 | 20 | 10 | 10 | |
| 3-M-1,3-BG[2]) | 10 | 15 | 5 | | | | | 10 | 10 | 10 | 10 | 10 | 15 | 5 | | | | |
| 1,3-Butylene glycol | | | | | 10 | | | | | | | | | | | 10 | | |
| Propylene glycol | | | | | | 10 | | | | | | | | | | | 10 | |
| pH — adjusting agent | | trace | | | trace | | | | trace | | | | trace | | | | | |
| Purified water | 75 | 75 | 75 | 75 | 75 | 75 | 95 | 79.5 | 79 | 78 | 70 | 80 | 80 | 80 | 80 | 80 | 80 | 100 |
| Conductance of skin sunface ($\mu\Omega^{-1}$) | 192 | 190 | 181 | 72 | 75 | 76 | 58 | 140 | 155 | 168 | 201 | 53 | 48 | 60 | 65 | 51 | 49 | 31 |

[1])The same as in 1) of Table 8
[2])The same as in 4) of Table 8
The compounding amount of purified water is shown as a value containing a trace of the pH — adjusting agent.

Example 28

Samples (cleansing type model cosmetics) were prepared according to the following basic formulations (see Table 10). Each sample was applied on skin and then washed away with water therefrom, the resultant skin surface was measured for conductance, and thereby the moisturizing effect of each sample on the skin was evaluated.

Process of Preparing Such a Sample

The component A was mixed into the component B under stirring at a temperature of 80° C., the component C was added by portions, and the mixture was cooled to 20° C.

Method of Measuring the Conductance of the Skin Surface

Such a sample was applied on the skin according to the method as described in Example 26, the applied skin surface was massaged and washed with water, the remaining water was wiped up, and the skin was measured for conductance at the time of a lapse of 60 minutes.

The formulation of each sample and the measured value of the conductance of the surface of the skin coated with each sample are shown in Table 10. As seen therefrom, in each of the model cosmetics of the invention (Sample Nos. 1 to 3), the conductance of the skin surface after the cleansing treatment was large, and thus moisturizing effect was not lowered. On the other hand, in the cases of water alone, an aqueous potassium laurate solution and a usual cleansing oil (Sample Nos. 4 to 6), the conductances of the skin surfaces after the cleansing treatment were small.

TABLE 10

(Compounding amounts of components: % by weight)

| | Sample No. | | | | | |
|---|---|---|---|---|---|---|
| | 1 | 2 | 3 | 4 | 5 | 6 |
| | Invention product | | | Comparative product | | |
| Component A | | | | | | |
| Purified hydrogenated soybean lecithin[1] | 2 | 2 | 2 | | | |
| Component B | | | | | | |
| Sorbitol 70[2] | 20 | 10 | 30 | | | |
| 3-M-1,3-BG[3] | 20 | 30 | 10 | | | |
| Component C | | | | | | |
| Isopropyl myristate | 58 | 58 | 58 | | | |
| Purified water | | | | 100 | | |
| Aqueous 10% potassium laurate solution | | | | | 100 | |
| Cleansing oil[4] | | | | | | 100 |
| Conductance of skin sunface ($\mu\Omega^{-1}$) | 52 | 56 | 53 | 31 | 21 | 26 |

[1]The same as in 1) of Table 8
[2]Aqueous 70% by weight sorbitol solution
[3]The same as in 4) of Table 8
[4]The composition is Tween 80: 5% by weight, Span 80: 5% by weight, liquid petrolatum: 40% by weight and isopropyl myristate: 50% by weight Example 29

Cream

A moisturizing cream was prepared by way of trial using the raw material components of the following (1) to (10). (1) to (3) were heated to 80° C. and mixed to give a moisturizing composition as a uniform solution. Separately, (4) to (9) were heated to 85° C. and mixed to give an oil phase. The oil phase was added by portions to the moisturizing composition at a temperature of 80° C. under stirring to give a viscous composition. (10) heated to 80° C. was poured in this viscous composition, and the mixture was stirred to give an emulsion and cooled to room temperature to give an oil-in-water type cream. This cream was one giving excellent moist touch to women of dry skin. When this cream was left alone in a room (20 to 25° C., a humidity of 40 to 60%, this is applied hereinafter) for 1 year, it had good stability without forming any separation of the components nor any deposit.

| | (% by weight) |
|---|---|
| (1) Sorbitol solution (70%) | 10 |
| (2) Purified hydrogenated soybean lecithin | 2 |
| (3) 3-methyl-1,3-butylene glycol | 5 |
| (4) Stearyl alcohol | 2 |
| (5) Microcrystalline wax | 2 |
| (6) Squalane | 5 |
| (7) Glyceryl trioctanoate | 10 |
| (8) Octyldodecyl myristate | 5 |

-continued

| | (% by weight) |
|---|---|
| (9) Methyl paraoxybenzoate | 0.3 |
| (10) Purified water | balance |
| Total | 100.0 |

Example 30

Liquid Cream

A liquid cream was prepared by way of trial using the raw material components of the following (1) to (11). (1) to (3) were heated to 80° C. and mixed to give a moisturizing composition as a uniform solution. Separately, (4) to (10) were heated to 85° C. and mixed to give an oil phase. The oil phase was added by portions to the moisturizing composition at a temperature of 80° C. under stirring to give a viscous composition. (11) heated to 80° C. was poured in this viscous composition, and the mixture was stirred to give a liquid cream and cooled to room temperature to give an oil-in-water type liquid cream. This liquid cream does not give a touch of incompatibility at the time of use, and even at the time of a lapse of one day after the use moist touch sufficiently remained, and the liquid cream was stable in the room for one year.

| | (% by weight) |
|---|---|
| (1) Glycerol | 8 |
| (2) Purified lecithin | 1 |
| (3) 3-methyl-1,3-butylene glycol | 10 |
| (4) Cetanol | 1 |
| (5) Candelilla wax | 1 |
| (6) Liquid petrolatum | 5 |
| (7) Isopropyl palmitate | 5 |
| (8) Isononyl nonanoate | 5 |
| (9) Methyl phenyl polysiloxane | 1 |
| (10) Ethyl paraoxybenzoate | 0.1 |
| (11) Purified water | balance |
| Total | 100.0 |

Example 31

Skin Lotion

A skin lotion was prepared by way of trial using the raw material components of the following (1) to (8). (1) to (6) were heated to 80° C. and mixed to give a moisturizing composition as a uniform solution. Separately, (7) and (8) were heated to 80° C. and mixed to give an aqueous solution. The aqueous solution was added by portions to the moisturizing composition at a temperature of 80° C. under stirring to give an isotropic solubilized liquid, and this was cooled to room temperature to give a skin lotion. This skin lotion had good touch at the time of use, and even at the time of a lapse of one day after the use moist touch remained, and the skin lotion was stable in the room for one year.

| | (% by weight) |
|---|---|
| (1) Glycerol | 10 |
| (2) Purified hydrogenated soybean lecithin | 5 |

-continued

| | (% by weight) |
|---|---|
| (3) 3-methyl-1,3-butylene glycol | 10 |
| (4) Purified water ① | 1 |
| (5) Squalane | 0.1 |
| (6) Ethyl paraoxybenzoate | 0.1 |
| (7) Quince seed gum | 0.1 |
| (8) Purified water ② | balance |
| Total | 100.0 |

Example 32

Skin Lotion 2

A skin lotion was prepared by way of trial using the raw material components of the following (1) to (8). (1) to (6) were heated to 80° C. and mixed to give a moisturizing composition as a uniform solution. Separately, (7) and (8) were heated to 80° C. and mixed to give an aqueous solution. The aqueous solution was added by portions to the moisturizing composition at a temperature of 80° C. under stirring to give a white turbid emulsion, and this was cooled to room temperature to give a skin lotion. This skin lotion had good touch at the time of use, and even at the time of a lapse of one day after the use moist touch sufficiently remained, and the skin lotion was stable in the room for one year.

| | (% by weight) |
|---|---|
| (1) Concentrated glycerol | 5 |
| (2) Diglycerol | 5 |
| (3) Purified hydrogenated egg yolk lecithin | 2 |
| (4) 3-methyl-1,3-butylene glycol | 10 |
| (5) Dicaprylic acid neopentyl glycol ester | 1 |
| (6) Ethyl paraoxybenzoate | 0.1 |
| (7) Sodium hyaluronate | 0.1 |
| (8) Water | balance |
| Total | 100.0 |

Example 33

Cleansing Gel

A cleansing gel was prepared by way of trial using the raw material components of the following (1) to (11). (1) to (5) were heated to 80° C. and mixed to give a moisturizing composition as a uniform solution. Separately, (6) and (11) were heated to 80° C. and mixed to give an oil phase. The oil phase was added by portions to the moisturizing composition at a temperature of 80° C. is under stirring to give a gel-like composiion, and this was cooled to room temperature to give a cleansing gel. This cleansing gel had excellent cleansing properties and good washing-away properties with water, and on the skin after the washing-away there was sufficient moist touch but little stretched touch.

| | (% by weight) |
|---|---|
| (1) Concentrated glycerol | 25 |
| (2) Purified hydrogenated soybean lecithin | 2 |
| (3) 3-methyl-1,3-butylene glycol | 10 |
| (4) Water | 2 |

-continued

| | (% by weight) |
|---|---|
| (5) Chamomile extract | 1 |
| (6) Squalane | 10 |
| (7) Liquid petrolatum | 10 |
| (8) Glyceryl trioctanoate | 20 |
| (9) Octyldodecyl myristate | 5 |
| (10) Isooctyl palmitate | 10 |
| (11) Jojoba oil | 5 |
| Total | 100.0 |

Example 34

Moisture Gel

A moisture gel was prepared by way of trial using the raw material components of the following (1) to (7). (1) to (3) were heated to 80° C. and mixed to give a moisturizing composition as a uniform solution. (4) heated to 80° C. was mixed into this, and a mixed solution of (5) to (7) was mixed thereinto to give a transparent moisture gel. This moisture gel had good stability, and moist touch in one day after the use thereof was extremely excellent.

| | (% by weight) |
|---|---|
| (1) Concentrated glycerol | 10 |
| (2) Purified hydrogenated soybean lysolecithin (hydrolysis degree 50%) | 5 |
| (3) 3-methyl-1,3-butylene glycol | 10 |
| (4) Aqueous 1% carboxyvinyl polymer solution | 40 |
| (5) Aqueous 1% potassium hydroxide solution | 10 |
| (6) Aqueous 10% sodium hyaluronate solution | 1 |
| (7) Water | balance |
| Total | 100.0 |

Example 35

Pack

A pack was prepared by way of trial using the raw material components of the following (1) to (10). (1) to (4) were heated to 80° C. and mixed to give a moisturizing composition as a uniform solution. Separately, (5) and (6) were added to (10) and made to be dispersed, the moisturizing composition was dispersed, and finally (7) to (9) were dispersed to give a muddy pack. This pack was excellent in the soft touch and wet touch of the skin after use.

| | (% by weight) |
|---|---|
| (1) Sorbitol | 10 |
| (2) Triglycerol | 10 |
| (3) Purified hydrogenated egg yolk lecithin | 5 |
| (4) 3-methyl-1,3-butylene glycol | 10 |
| (5) Montmorillonite | 1 |
| (6) Ethanol | 5 |
| (7) Titanium oxide | 5 |
| (8) Kaolin | 10 |
| (9) Talc | 5 |
| (10) Purified water | balance |
| Total | 100.0 |

Example 36

Emulsion Foundation

An emulsion foundation was prepared by way of trial using the raw material components of the following (1) to (14). (1) to (4) were heated to 80° C. and mixed to give a moisturizing composition as a uniform solution. Separately, (9) to (13) were heated to 85° C. and mixed to give an oil phase. The oil phase was added by portions to the moisturizing composition at a temperature of 80° C. under stirring to give a viscous composition. (14) heated to 80° C. was poured into this viscous composition, the mixture was stirred to give an emulsion, (5) to (8) were dispersed thereinto, and the mixture was cooled to room temperature to give an emulsion foundation. This emulsion foundation was such that there was extremely little dry touch on the skin after the use and wiping-up thereof.

|  | (% by weight) |
|---|---|
| (1) Concentrated glycerol | 10 |
| (2) Purified hydrogenated soybean lecithin | 1 |
| (3) 3-methyl-1,3-butylene glycol | 10 |
| (4) Purified water ① | 5 |
| (5) Talc | 3 |
| (6) Titanium oxide | 5 |
| (7) Red oxide | 0.5 |
| (8) Yellow iron oxide | 1 |
| (9) Liquid petrolatum | 5 |
| (10) Cetyl octanoate | 10 |
| (11) Octyldodecyl lactate | 3 |
| (12) Lanolin | 2 |
| (13) Cetanol | 2 |
| (14) Purified water ② | balance |
| Total | 100.0 |

Example 37

Bath

A bath was prepared by way of trial using the raw material components of the following (1) to (9). (1) to (6) were heated to 80° C. and mixed to give a moisturizing composition as a uniform solution. Separately, (7) to (9) were heated to 80° C. and mixed to give an oil phase. The oil phase was added by portions to the moisturizing composition at a temperature of 80° C. under stirring to give a gel-like composition, and this was cooled to room temperature to give a white turbid bath. After bathing using this bath, the moist touch of the skin sufficiently remained and there was no sticky touch.

|  | (% by weight) |
|---|---|
| (1) Concentrated glycerol | 30 |
| (2) Purified hydrogenated soybean lecithin | 2 |
| (3) 3-methyl-1,3-butylene glycol | 10 |
| (4) Chamomile extract | 2 |
| (5) Ligusticum extract | 2 |
| (6) Calamus extract | 1 |
| (7) Liquid petrolatum | 10 |
| (8) Glyceryl trioctanoate | 38 |
| (9) Methyl phenyl polysiloxane | 5 |
| Total | 100.0 |

Example 38

Ointment

An ointment was prepared by way of trial using the raw material components of the following (1) to (12). (1) to (4) were heated to 80° C. and mixed to give a moisturizing composition as a uniform solution. Separately, (5) to (11) were heated to 85° C. and mixed to give an oil phase. The oil phase was added by portions to the moisturizing composition at a temperature of 80° C. under stirring to give a viscous composition. (12) heated to 80° C. was poured into this viscous composition, the mixture was stirred to give an emulsion, and the emulsion was cooled to room temperature to give a hydrophilic ointment. This ointment was one which is liable to get to fit the skin and gives moist touch thereto, and was excellent in stability without the separation of the components in the room for one year.

|  | (% by weight) |
|---|---|
| (1) Glycerol | 10 |
| (2) Purified hydrogenated soybean lecithin | 1 |
| (3) 3-methyl-1,3-butylene glycol | 15 |
| (4) Purified water ① | 5 |
| (5) Glyceryl monostearate | 1 |
| (6) Stearyl alcohol | 5 |
| (7) Petrolatum | 10 |
| (8) Isopropyl myristate | 10 |
| (9) Propyl paraoxybenzoate | 0.1 |
| (10) Methyl paraoxybenzoate | 0.1 |
| (11) Glycyrrhetinic acid | 0.3 |
| (12) Purified water ② | balance |
| Total | 100.0 |

Example 39

Gel

A gel was prepared by way of trial using the raw material components of the following (1) to (9). Namely, (1) to (3) were heated to 80° C. and mixed to give a moisturizing composition as a uniform solution. Separately, a mixed solution of (4) to (6) heated to 80° C. was mixed with the moisturizing composition, the mixture was cooled, and (7) to (9) were added respectively to give a gel. This gel had good touch at the time of use and gave moist touch and wet touch on the skin, and was excellent in stability without the separation of the components, any deposit and the occurrence of foul smells in the room for one year.

|  | (% by weight) |
|---|---|
| (1) Glycerol | 20 |
| (2) Purified hydrogenated egg yolk lecithin | 10 |
| (3) 3-methyl-1,3-butylene glycol | 20 |
| (4) Polyethylene glycol 400 | 20 |
| (5) Aqueous 10% carboxyvinyl polymer solution | 4 |
| (6) Aqueous 10% sodium hydroxide solution | 1 |
| (7) Ethanol | 2 |
| (8) Dipotassium glycyrrhetinate | 0.3 |
| (9) Water | balance |
| Total | 100.0 |

INDUSTRIAL APPLICABILITY

The moisturizing composition of the invention has an action to make slower the evapotranspiration of moisture under a low humidity condition accompanied by the lowering of the equilibrium moisture, which has been a problem in polyhydric alcohols known as moisturizing agents, and exerts an effective function as a moisturizing agent even under low humidity environments. Compositions obtained using this moisturizing agent can take various forms such as viscous form, gel-like form, oil-in-water type emulsion form and solubilized form, and thus can be used as bases for various products wherein these forms and the moisturizing characteristic are utilized, and have extremely wide applicability.

The cosmetic or external preparation of the invention contains a moisturizing composition comprising the above-mentioned specific components, and are excellent in moisturizing properties. Touch at the time of use and after use is also good. The cosmetic or external preparations can be prepared as various forms such as viscous form, gel-like form, oil-in-water type emulsion form and solubilized form, and are rich in stability.

What is claimed is:

1. A moisturizing composition consisting essentially of:
   (a) a trihydric or more water soluble polyhydric alcohol,
   (b) lecithin, and
   (c) 3-methyl-1,3-butylene glycol,
   wherein the weight ratio of (b) to the total of (a) and (c) is from 1:1,000 to 1:1 and the weight ratio of (a) to (c) is 1:10 to 20:1 wherein the composition has polarizability.

2. The moisturizing composition according to claim 1 which further contains water in an amount of more than 0% by weight up to 50% by weight of the total weight of the total of (a), (b) and (c).

3. The moisturizing composition according to claim 1 wherein the trihydric or more water soluble polyhydric alcohol is glycerol and/or sorbitol.

4. The moisturizing composition according to claim 1 wherein lecithin is hydrogenated lecithin.

5. A viscous or gel base comprising the moisturizing composition according to claim 1 having an oily substance, excluding 1,3-butane diol, compounded therein.

6. An oil-in-water emulsion base comprising the moisturizing composition according to claim 1 having an oily substance, excluding 1,3-butane diol, and water compounded therein.

7. A solubilized base comprising the moisturizing composition according to claim 1 diluted with water.

8. A cosmetic comprising the moisturizing composition according to claim 1 and at least another cosmetic material, excluding 1,3-butane diol, therein.

9. A topical composition comprising the moisturizing composition according to claim 1 and at least one other component, excluding 1,3-butane diol, for a topically applied composition.

* * * * *